United States Patent [19]
Havera et al.

[11] 3,995,041
[45] Nov. 30, 1976

[54] DERIVATIVES OF 2-SUBSTITUTED-HYDROXYANILINO-HEXAHYDRO-2H-BENZO[α]QUINOLIZINES

[75] Inventors: Herbert John Havera, Edwardsburg, Mich.; Richard Don Johnson, Elkhart, Ind.; Horacio Vidrio, Mexico City, Mexico

[73] Assignee: Miles Laboratories, Inc., Elkhart, Ind.

[22] Filed: Oct. 30, 1975

[21] Appl. No.: 627,063

[52] U.S. Cl. .................. 424/258; 260/286 R; 260/287 CF; 260/288 D
[51] Int. Cl.² ................................. C07D 217/22
[58] Field of Search...... 260/286 CF, 286 R, 288 D; 424/258

[56] References Cited
UNITED STATES PATENTS
3,634,431  1/1972  Van Dyke ............... 260/286 CF
3,635,986  1/1972  Van Dyke ............... 260/286 CF OTHER PUBLICATIONS
Van Dyke et al., J. Med. Chem., vol. 15, (1972) pp. 91–94.

Primary Examiner—Paul M. Coughland, Jr.
Attorney, Agent, or Firm—Myron B. Sokolowski

[57] ABSTRACT

2-Substituted-hydroxyanilino-hexahydro-2H-benzo[α]quinolizines of the structural formula,

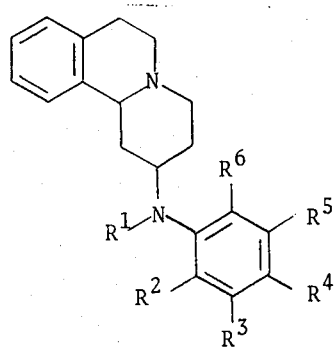

in which $R^1$ is a hydrogen atom or an alkanoyl group of 2 to 4 carbon atoms and each of substituents $R^2$, $R^3$, $R^4$, $R^5$, and $R^6$ is a hydrogen atom, a hydroxyl, or a methyl group, such that at least one of the latter substituents is a hydroxyl group, exhibit coronary vasodilating activity.

20 Claims, No Drawings

DERIVATIVES OF 2-SUBSTITUTED-HYDROXYANILINO-HEXAHYDRO-2H-BENZO[α]QUINOLIZINES

BACKGROUND OF THE INVENTION

1. Field

The derivatives of 2-substituted-hydroxyanilino-hexahydro-2H-benzo[α]quinolizines described in this specification are useful in the treatment of ischemic heart diseases or of other cardiac disorders in which coronary vasodilation is indicated.

2. Prior Art

The prior art relevant to the compounds of this invention includes: U.S. Pat. No. 3,634,431, issued to J. W. Van Dyke on Jan. 11, 1972 ("Van Dyke I"); U.S. Pat. No. 3,635,986, issued to J. W. Van Dyke on Jan. 18, 1972 ("Van Dyke II"); and "Cardiovascular Activity of Some Substituted-2-Amino-Benzoquinolizines," by J. W. Van Dyke et al. in: J. Med Chem, 15:91 (1972) ("Van Dyke III").

The cited references collectively disclose compounds having the generic structural formula I,

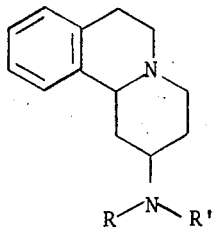

in which R is a hydrogen atom or an alkanoyl group and R' is a phenyl, methyl-substituted phenyl, or methoxy-substituted phenyl group. Van Dyke III reports the synthesis and biological activity of 2-(4-methoxyanilino)-1,3,4,6,7,11β-hexahydro-2H-benzo[α]-quinolizine dihydrochloride; that compound has the structure,

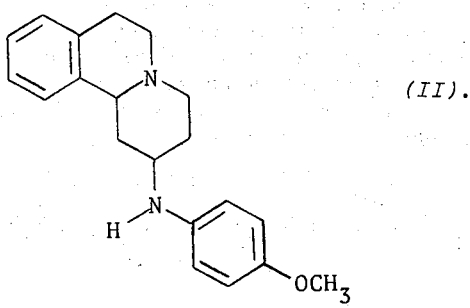

Compound II possesses structural similarity but qualitative and quantitative differences in pharmacological properties than the compounds of the present invention. Comparison of the latter and II is provided in the succeeding SUMMARY OF THE INVENTION and in following Example 11.

SUMMARY OF THE INVENTION

The subject matter of this invention is:

1. coronary-vasodilating compounds and pharmacologically acceptable, non-toxic, acid salts thereof having the generic structure III,

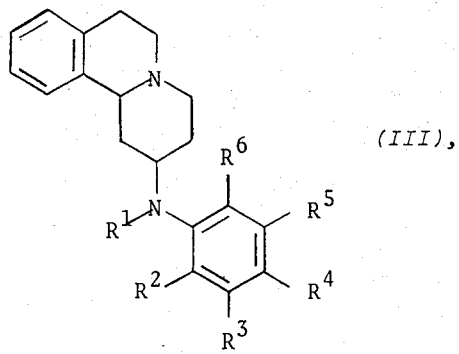

in which $R^1$ is a hydrogen atom or an alkanoyl group of 2 to 4 carbon atoms and each of substituents $R^2$, $R^3$, $R^4$, $R^5$, and $R^6$ is a hydrogen atom, a methyl, or a hydroxyl group, provided that at least one of substituents $R^2$–$R^6$ is a hydroxyl group; and (2) a therapeutic method of selectively producing coronary vasodilation in an individual in whom that therapy is indicated by use of compounds III.

Compounds III exhibit a specific coronary-vasodilating effect in an individual without a concommitant effect in the peripheral circulation (the term "individual" defines a human being in whom coronary vasodilation is therapeutically indicated or a standard laboratory-animal used as an experimental model thereof); it is that property of compounds III which distinguishes them over the compounds revealed in the prior art. None of the cited references discloses hydroxyl-substituted compounds having formula III. Van Dyke I and II simply state that the prior art compounds I are antihypertensive agents (which thus affect peripheral blood flow) but provide no pharmacological data to confirm the stated utility. Van Dyke III, on the other hand, demonstrates that some species of I possess peripheral vasodilating activity, that others exhibit coronary vasodilating properties, and that still others display both coronary and peripheral vasodilating activity. Of particular interest in the latter category is 2-(4-methoxyanilino)-1,3,4,6,7,11β-hexahydro-2H-benzo[α]quinolizine (compound II, supra; see Van Dyke III: Table I [compound 36 therein], page 92, and Table 2, page 93). Example 11 of the instant specification demonstrates that while II produces peripheral vasodilation at a dose of 1 mg/kg in anesthetized dogs which continues for 60 minutes or more, it produces a rather weak increase in coronary bloodflow which totally dissipates after 10 minutes. In contradistinction, the compounds of this invention, III, display a reciprocal effect under similar conditions: they produce a strong increase in coronary bloodflow which is maintained for at least 60 minutes and a weak peripheral vasodilation which does not exceed 20 minutes in duration. Compounds III therefore act specifically on coronary vasculature, while the structurally similar prior art compound II displays specificity as a peripheral vasodilator.

Synthesis of compounds III proceeds via the preferred pathway outlined in Table I; that synethsis is a modification of the process reported in Van Dyke I–III.

Reaction (step A) of 1,3,4,6,7,11α-hexahydro-2H-benzo[α]quinolizin-2-one, IV, with an appropriately substituted aniline, V, in the presence of a catalytic amount of p-toluenesulfonic acid in benzene at steam bath temperatures yields the Schiff-base intermediate, VI. In V, each of substituents $R'^2$ through $R'^6$ is a hydrogen atom, a methyl or a benzoloxy group but at least one of those substituents must be a benzyloxy group. Reduction (step B) of VI with sodium borohydride in methanol at ice bath temperatures provides the amine, VII.

Free bases of III are converted to corresponding acid addition salts by conventional methods. Pharmacologically acceptable, non-toxic, acid addition forms of III include but are not limited to the hydrochloride, hydrobromide, oxadate, succinate, formate, acetate, and maleate salts.

Administration of a compound of structural formula III by conventional means selectively produces coronary vasodilation without attendant peripheral effects in individuals in whom coronary vasodilation is indicated therapeutically. The term "conventional means"

TABLE I

SYNTHESIS OF 2-HYDROXYANILINO-HEXAHYDRA[α]QUINOLIZINES

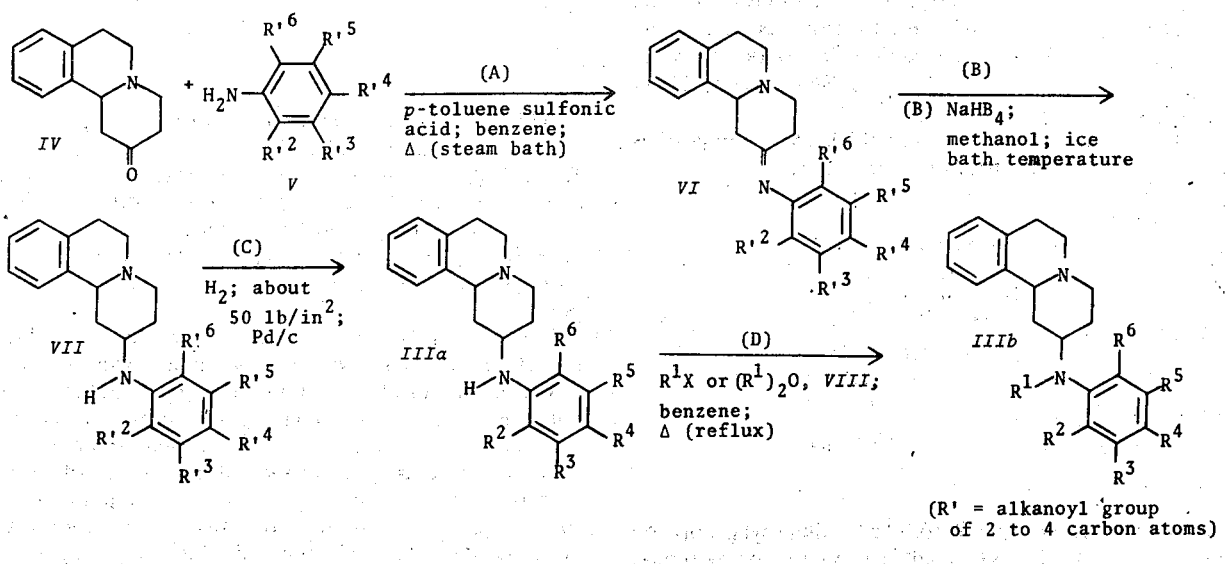

(R' = alkanoyl group of 2 to 4 carbon atoms)

Hydrogenation (step C) of VII under pressure (about 50 pounds/inch²) in the presence of catalyst (palladium/carbon) affords respective 2-substituted-hydroxyanilino-hexahydro-2H-benzo[α]quinolizines, IIIa, in which substituents $R^2$–$R^6$ have the same definition as in III, supra. Acylation (step D) of IIIa with a desired alkanoyl halide or anhydride, VIII, in benzene under reflux yields congeners, IIIb.

Starting compounds IV, V, and VIII have been reported in the relevant literature or are commercially available. Beke and Szantay (Chem. Ber. 95:2132 [1962]) disclose the synthesis of 1,3,4,6,7,11β-hexahydro-2H-benzo[α]quinolizin-2-one, IV; that synthesis involves the condensation of 3,4-dihydro-isoquinoline hydrochloride and methyl vinyl ketone, both of which are commercially available. Compounds V and VII are also readily available and appear in the relevant literature. Representative of V are: 2-benzyloxyaniline; 3-benzyloxyaniline; 4-benzyloxyaniline; 2,4-dibenzyloxyaniline; 3,4-dibenzyloxyaniline; 2,4,6,-tribenzyloxyaniline; 2-methyl-4-benzyloxyaniline; 3-methyl-4-benzyloxyaniline; 2,6-dimethyl-4-benzyloxyaniline; and 2,3,5,6-tetramethyl-4-benzyloxyaniline. Representative of VII are acetic, propionic, and butyric halides or anhydrides.

denotes oral, intravenous, intramuscular, subcutaneous, sublingual, buccal, rectal, and other recognized modes of administration of therapeutic agents. Compounds III may be administered in either liquid or solid form depending on the vehicle utilized. Dosages may vary depending upon the physiological requirements of a given individual and may be determined without undue experimentation by one skilled in the field.

The succeeding examples provide preferred embodiments of the disclosed inventions.

DESCRIPTION OF THE PREFERRED EMBODIMENTS

Example 1

2-(4-Hydroxyanilino-1,3,4,6,7,11β-hexahydro-2H-benzo[α]-quinolizine monoxalate monohydrate (TR 3131).

Para-aminophenol (2.75 g; 0.025 M) and a catalytic amount of p-toluenesulfonic acid was added to a solution of 1,3,4,6,7,11β-hexahydro-2-H-benzo[α]quinolizine-2-one (5.0 g; 0.025 M) in 100 ml of dry toluene. The mixture was heated under reflux using a Dean- Stark trap to remove water. After the calculated amount of water was removed, the solution was evaporated in vacuo to obtain an oily residue. That residue was dissolved in 50 ml of MeOH and NaBH$_4$ (2.0 g) was added slowly while the reaction was stirred in an ice bath. The solution then was heated under reflux, stirring for 1 hour. The resulting solution wwas evaporated in vacuo and the residue was taken up in water and Et$_2$0. The Et$_2$O was evaporated in vacuo yielding an oily residue. The oxalate salt was prepared on the oil by adding 2.7 g of oxalic acid to the 8.0 g of free base. Upon addition of Et$_2$O, a solid precipitated which was recrystallized from H$_2$O, MeOH and DMF to give a white solid (3.0 g), m.p. 155°–165° C.

ANALYSIS: Calculated for $C_{21}H_{26}N_2O_6$: C, 62.68; H, 6.51; N, 6.97. Found: C, 63.01; H, 6.56; N, 7.01.

Example 2

2-(4-Hydroxyanilino)-1,3,4,6,7,11β-hexahydro-2H-benzo[α]quinolizine dihydrochloride (TR 3273).

A solution of 1,3,4,6,7,11β-hexahydro-2H-benzo[α]-quinolizine-2-one (10.0 g; 0.05 M), 4-benzyloxyaniline (12.0 g; 0.06 M), and a catalytic amount of p-toluenesulfonic acid in 250 ml of benzene was heated on a steam-bath (1.5 hours) using a Dean-Stark Trap to remove water (0.9 ml). The solvent was evaporated in vacuo yielding the crude imine as an orange solid. The imine was suspended in MeOH (200 ml) and was stirred in an ice-bath as NaBH$_4$ (10.0 g) was added portionwise. After 1 hour the ice-bath was removed and the reaction mixture slowly exothermed to reflux temperature. After cooling, the mixture was filtered to give a tan solid (16.5 g) of ill-defined melting point (circa 80° C). That tan solid was dissolved in a mixture of Et$_2$O (500 ml) and CHCl$_3$ then stirred with activated carbon and filtered. To the filtrate was added two equivalents of HCl in isopropyl alcohol, and the resulting precipitate was recovered by filtration and was recrystallized twice from MeOH giving a white solid (10.0 g) m.p. 252°–253° C.

ANALYSIS: Calculated for $C_{26}H_{30}Cl_2N_2O$: C, 68.26; H, 6.61; N, 6.13. Found: C, 67.29; H, 6.61; N, 6.17.

To a solution of that white solid (8.0 g) in 250 ml of MeOH was added 1.0 g of 10% Pd/C. The resulting mixture was hydrogenated at 50 pounds/inch$^2$ and the calculated amount of H$_2$ was taken up in 24 hours. The catalyst was removed by filtration and the filtrate was evaporated in vacuo. The resulting residue was crystallized from a mixture of MeOH and Et$_2$O to give an off-white solid (5.7 g) m.p. 286°–287° C.

ANALYSIS: Calculated for $C_{19}H_{24}Cl_2N_2O$: C, 62.13; H, 6.58; N, 7.62. Found: C, 61.32; H, 6.65; N, 7.39.

Example 3

2-(2,4-Dihydroxyanilino)-1,3,4,6,7,11β-hexahydro-2H-benzo[α]quinolizine dihydrobromide hydrate (TR 3210).

A solution of 1,3,4,6,7,11β-hexahydro-2H-benzo[α]-quinolizin-2-one (40.2 g, 0.2 mole), 2,4-dimethoxyaniline (33.7 g, 0.22 mole) and a catalytic amount of p-toluene-sulfonic acid in 500 ml of benzene was heated at reflux for 20 hours using a Dean-Stark trap to remove water (3.6 ml). The solvent was evaporated in vacuo to give the crude imine as a dark oil. The imine was dissolved in 500 ml of MeOH and cooled in an ice bath. NaBH$_4$ (16.0 g) was added to the cold solution in small portions with stirring. When bubbling had ceased, the solution was warmed to room temperature, then heated to reflux for 1 hour. Upon cooling to room temperature a solid crystallized from solution. The mixture was cooled in an ice bath, and the solid removed by filtration to give 36.8 g of a white solid which melted at 116°–118° C.

ANALYSIS: Calculated for $C_{21}H_{26}N_2O_2$: C, 74.53; H, 7.74; N, 8.28. Found: C, 74.21; H, 7.88; N, 8.11.

A sample of the white solid (3.4 g; 0.01 mole) and 40 ml of 48% HBr was heated to reflux for 20 hours. The excess 48% HBr was evaporated in vacuo and the resulting residue was crystallized from isopropyl alcohol to give 4.8 g of a purple solid which decomposed above 250° C. Recrystallization from MeOH gave 1.3 g of a solid which softens at 248° C and decomposes at 289°–292° C.

ANALYSIS: Calculated for $C_{19}H_{26}Br_2N_2O_3$: C, 46.54; H, 5.35; N, 5.72. Found: C, 46.84; H, 5.34; N, 5.62.

Example 4

2-(3-Hydroxyanilino)-1,3,4,6,7,11β-hexahydro-2H-benzo[α]quinolizine dihydrochloride (TR 3245).

A solution of 1,3,4,6,7,11β-hexahydro-2H-benzo[α]-quinolizin-2-one (10 g, 0.05 mole), 3-benzyloxyaniline (10 g, 0.05 mole) and a catalytic amount of p-toluenesulfonic acid in 250 ml of benzene was heated to reflux for 20 hours using a Dean-Stark trap to remove water (0.9 ml). The solvent was evaporated in vacuo to give the crude imine as an oil. The imine was dissolved in 250 ml of MeOH and cooled in an ice bath. NaBH$_4$ (5 g) was added to the solution in small portions with stirring. When the bubbling had ceased, the solution was warmed to room temperature, then heated to reflux for 2 hours. The solvent was evaporated in vacuo and the resulting residue was stirred with water then extracted with CHCl$_3$. The combined CHCl$_3$ extracts were washed with water, saturated HaHCO$_3$, and saturated NaCl. The CHCl$_3$ extracts were dried over MgSO$_4$ and evaporated in vacuo to give an oil. The oil was dissolved in isopropyl alcohol to which solution of HCl in isopropyl alcohol (50 ml of 3.32N) was added. The addition of EtOAc produced an oil which did not crystal. The solvent was evaporated in vacuo and the resulting dark residue was dissolved in warm MeOH. Et$_2$O was added until the solution became cloudy. An oil, which crystallized slowly, separated. Recrystallization from a mixture of MeOH and Et$_2$O and then from MeOH gave a white solid, yield of 4.0 g, mp 223°–226° C.

ANALYSIS: Calculated for $C_{26}H_{30}Cl_2N_2O$: C, 68.26; H, 6.61; N, 6.13. Found: C, 67.60; H, 6.74; N, 6.02.

The white solid (4 g) was dissolved in MeOH (250 ml) to which 10% Pd/C (0.5 g) was added. The mixture was hydrogenated at 50 pounds/inch$^2$. The theoretical amount of H$_2$ was taken up. The catalyst was removed by filtration, and the filtrate was evaporated in vacuo to give a viscous residue. The residue was crystallized from isopropyl alcohol to give a solid which was recrystallized from MeOH; yield 1.0g; mp 283°–284° C.

ANALYSIS: Calculated for $C_{19}H_{24}Cl_2N_2O$: C, 62.13; H, 6.58; N, 7.62. Found: C, 62.04; H, 6.71; H, 7.71.

Example 5

N-(4-Hydroxyphenyl)-N-(1,3,4,6,7,11β-hexahydro-2H-benzo[α]quinolizin-2-yl)propionamide hydrochloride (TR 3310).

A crude sample of 2-(4-benzyloxyanilino)-1,3,4,6,7,11β-hexahydro-2H-benzo[α]quinolizine was prepared by the method described in Example 2. This tan solid (15.5 g; 0.04 mole) was added to a solution of propionic anhydride (5.3 g; 0.04 mole) in 250 ml of benzene, and the resulting solution was heated at reflux for 24 hours. The solvent was evaporated in vacuo; the residue stirred with 400 ml of 20% NaOH; then extracted with $CHCl_3$ (4×150 ml). The combined $CHCl_3$-extracts were washed with water (100 ml) and saturated NaCl (200 ml), dried ($MgSO_4$), and evaporated in vacuo to give a dark oil (19.7 g). The oil was dissolved in isopropyl alcohol and one equivalent of HCl in isopropyl alcohol was added. Addition of EtOAc to the boiling isopropyl alcohol solution resulted in the formation of a precipitate. The mixture was cooled and the tan precipitate removed by filtration. The resulting tan solid was recrystallized first from isopropyl alcohol then twice from a mixture of MeOH and $Et_2O$ to give a white solid (5.1 g); m.p. 247°–253° C.

ANALYSIS: Calculated for $C_{29}H_{33}ClN_2O_2$: C, 73.00; H, 6.97; N, 5.87. Found: C, 72.34; H, 7.04; N, 5.94.

To a solution of the white solid (4.5 g) in 200 ml of MeOH was added 1.0 f of 10% Pd/C. The resulting mixture was hydrogenated at 50 pounds/inch$^2$ and the calculated amount of $H_2$ was taken up in 24 hours. The catalyst was removed by filtration and the filtrate was evaporated in vacuo. The resulting residue was crystallized from a mixture of isopropyl alcohol and EtOAc then recrystallized from a mixture of MeOH and $Et_2O$ to give a white solid (1.2 g) m.p. 257°–260° C.

ANALYSIS: Calculated for $C_{22}H_{27}ClN_2O_2$: C, 68.30; H, 7.03; N, 7.24. Found: C, 68.28; H, 6.87; N, 7.13.

Example 6

2-(2-Hydroxyanilino)-1,3,4,6,7,11β-hexahydro-2H-benzo[α]-quinolizine dihydrochloride (TR 3324).

A solution of 1,3,4,6,7,11β-hexahydro-2H-benzo[α]-quinolizine-2-one (10.0 g; 0.05 mole), 2-benzyloxyaniline (12.0 g; 0.06 mole), and a catalytic amount of p-toluene-sulfonic acid in 200 ml of toluene was heated at reflux (6 hours) using a Dean-Stark trap to remove water (0.09 ml). The solvent was evaporated in vacuo to give the crude imine as a dark oil. The imine was dissolved in MeOH (200 ml) and stirred in an ice-bath as $NaBH_4$ (10.0 g) was added portionwise. After 1 hour, the ice-bath was removed and the reaction mixture heated at reflux for 2 hours. The solvent was evaporated in vacuo and the residue was stirred with a mixture of water (200 ml) and $Et_2O$ (200 ml). The resulting two layers were separated and the aqueous layer extracted with $Et_2O$. The combined $Et_2O$ extracts were washed with water (2×100 ml) and saturated NaCl (2×100 ml) then dried ($MgSO_4$) and evaporated in vacuo giving a dark oil. The oil was dissolved in MeOH, and two equivalents of HCl in MeOH was added. The resulting dark solution was concentrated by boiling, and EtOAc was added. Upon cooling a precipitate formed which was removed by filtration to give 8.0 g of a white solid which slowly melts above 165° C. Recrystallization from isopropyl alcohol gave a white solid (6.0 g) which slowly melted above 165° C.

ANALYSIS: Calculated for $C_{26}H_{32}Cl_2N_2O_2$: C, 65.68; H, 6.78; N, 5.89. Found: C, 65.86; H, 6.86; N, 5.84.

Efforts to obtain the anhydrous salt by subsequent recrystallizations and drying resulted in obtaining the monohydrochloride monohydrate (3.4 g) from a mixture of isopropyl alcohol and EtOAc. This off-white solid slowly melts above 168° C.

ANALYSIS: Calculated for $C_{26}H_{31}ClN_2O_2$: C, 71.14; H, 7.12; N, 6.38. Found: C, 71.54; H, 6.92; N, 6.43.

To a solution of 2-(2-benzyloxyanilino)-1,3,4,6,7,11β-hexahydro-2H-benzo[α]quinolizine dihydrochloride monohydrate (7.0 g) in 300 ml of MeOH was added 1.0 g of 10% Pd/C. The resulting mixture was hydrogenated at 50 pounds/inch$^2$ and the calculated $H_2$ was taken up in 24 hours. The catalyst was removed by filtration and the filtrate was evaporated in vacuo to give a red oil. The oil was dissolved in isopropyl alcohol and the resulting solution was concentrated by boiling until a precipitate began to form. The mixture was cooled and filtered to give a pink solid (3.0 g) which was then triturated with hot isopropyl alcohol to give an off-white solid (2.2 g) which slowly melts with decomposition above 225° C.

ANALYSIS: Calculated for $C_{19}H_{24}Cl_2NO$: C, 62.13; H, 6.58; N, 7.62. Found: C, 61.91; H, 6.76; N, 7.73.

Example 7

2-(2,6-Dihydroxyanilino)-1,3,4,6,7,11β-hexahydro-2H-benzo-[α]quinolizine hydrochloride A mixture of 2-nitroresorcinol (63.5 g; 0.41 mole), benzyl bromide (140.3 g; 0.82 mole), and $K_2CO_3$ (113.4 g; 0.82 mole) in 1 L of dry acetone was stirred at reflux temperature for 48 hours. Approximately 400 ml of acetone was removed by distillation, and 1 L of 10% NaOH was added. The remaining acetone was removed by distillation, and the reaction mixture was then cooled and filtered to obtain a dark solid (146.0 g) m.p. 67°–74° C. The solid was dissolved in hot $CHCl_3$, treated with activated carbon, then filtered. The filtrate was evaporated in vacuo to give a yellow oil (141.0 g) which crystallized on standing. The solid was recrystallized from a mixture of $Et_2O$ and petroleum ether to give pale yellow crystals (87.3 g), m.p. 80° C. A sample (10.0 g) was again recrystallized from a mixture of $Et_2O$ and petroleum ether to give pale yellow crystals (7.7 g), m.p. 80° C.

ANALYSIS: Calculated for $C_{20}H_{17}NO_4$: C, 71.62; H, 5.11; N, 4.18. Found: C, 72.25; H, 5.24; N, 4.12.

Raney nickel (10.0 g) was added to a suspension of the yellow crystals (33.6 g; 0.1 mole) in 200 ml of anhydrous EtOH. The resulting mixture was hydrogenated at 50 pounds/inch$^2$ and the calculated $H_2$ was taken up in 2 hours. The catalyst was removed by filtration, and the filtrate was cooled in an ice-bath. The white needles which formed were removed by filtration to give 17.8 g, m.p. 70°–71° C. The infrared and nuclear magnetic resonance spectra were those expected for 2,6-bisbenzyloxyaniline. A solution of 1,3,4,6,7,11β-hexahydro-2H-benzo[α]quinolizine-2-one (10.0 g; 0.05 mole), 2,6-bisbenzyloxyaniline (15.3 g; 0.05 mole), and a catalytic amount of p-toluenesulfonic acid in 200 ml of toluene was heated at reflux for 24 hours using a Dean-Stark trap to remove water. The infrared spectrum of the reaction mixture exhibits carbonyl absorption (1720 cm$^{-1}$) which did not disappear when the reaction mixture was refluxed an additional 24 hours. The solvent was evaporated in vacuo giving a red oil. The infrared spectrum of the red oil exhibits a strong imine band at 1660 cm$^{-1}$ in addition to the weak carbonyl band at 1720 cm$^{-1}$. The oil was dissolved in MeOH (200 ml) and stirred in an ice-bath as $NaBH_4$ (10.0 g) was added portionwise. After 1 hour, the ice-bath was removed and the reaction mixture was heated at reflux for 1 hour. The solvent was evaporated in vacuo, the resulting residue was stirred with 300 ml of water, and the mixture was extracted with $Et_2O$ (3×200 ml). The combined $Et_2O$ extracts were washed with 20% NaOH (2×100 ml), H$_2$O (2×100 ml), and saturated NaCl (2×100 ml); dried (MgSO$_4$); and evaporated in vacuo to give a dark oil (26.0 g). The oil was dissolved in isopropyl alcohol and two equivalents of HCl in isopropyl alcohol was added. The resulting solution was concentrated by boiling, and upon cooling the hydrochloride salt of 2,6-bisbenzyloxyaniline precipitated as a white solid which was removed by filtration to give 6.0 g; m.p. 191°–193° C.

ANALYSIS: Calculated for C$_{20}$H$_{20}$ClNO$_2$: C, 70.28; H, 5.89; N, 4.10. Found: C, 69.95; H, 5.84; N, 4.14.

The isopropyl alcohol filtrate was successively concentrated, cooled, and filtered until the 2,6-bisbenzyloxyaniline failed to precipitate. A large volue of EtOAc was added to the isopropyl alcohol filtrate and a dark oil separated from solution. The supernate was decanted away from the dark oil. The oil was boiled in water, cooled, and filtered to give a beige solid which was recrystallized twice from aqueous MeOH giving a beige solid (5.2 g); m.p. 240°–241° C.

ANALYSIS: Calculated for C$_{33}$H$_{35}$ClN$_2$O$_2$: C, 75.20; H, 6.69; N, 5.32. Found: C, 74.58; H, 6.76; N, 5.10.

To a solution of the beige solid (4.5 g) in 200 ml of DMF was added 1.0 g of 10% Pd/C. The resulting mixture was hydrogenated at 50 pounds/inch$^2$ with heating. The calculated H$_2$ was taken up in 24 hours. The catalyst was removed by filtration, and the solvent was evaporated in vacuo to give a solid residue. The solid was dissolved in MeOH, the resulting solution was boiled, and isopropyl alcohol was added to replace the MeOH. A solid precipitated in the boiling isopropyl alcohol solution, and the hot mixture was filtered to give a beige solid (1.8 g); m.p. 262°–264° C.

ANAYLSIS: Calculated for C$_{19}$H$_{23}$ClN$_2$O$_2$: C, 65.79; H, 6.66N, 8.07. Found: C, 65.65; H, 7.06; N, 8.20.

Example 8

2-(2,3,5,6-Tetramethyl-4-hydroxyanilino)-1,3,4,6,7,11$\beta$-hexahydro-2H-benzo[$\alpha$]quinolizine dihydrochloride monohydrate (TR 3352).

A solution of 1,3,4,6,7,11$\beta$-hexahydro-2H-benzo[$\alpha$]quinolizine-2-one (7.6 g; 0.038 mole), 2,3,5,6-tetramethyl-4-hydroxyaniline (6.3 g; 0.038 mole), and a catalytic amount of p-toluenesulfonic acid in 200 ml of benzene was heated at reflux (24 hours) using a Dean-Stark trap to remove water. The reaction mixture was cooled then filtered to obtain the imine as light orange crystals (9.7 g), m.p. 211°–215° C. The imine (9.7 g) was suspended in 200 ml of MeOH and stirred in an ice-bath, as NaBH$_4$ (10.0 g) was added portionwise. The resulting solution was stirred an additional hour in the ice-bath then heated at reflux for 1 hour. The solvent was evaporated in vacuo, and the resulting residue was stirred with a mixture of water (200 ml) and CHCl$_3$ (200 ml). The resulting two layers were separated and the aqueous layer extracted with CHCl$_3$ (3×100 ml). The combined CHCl$_3$-extracts were dried (MgSO$_4$) and evaporated in vacuo to give a yellow oil (12.0 g). The oil was dissolved in isopropyl alcohol (150 ml), and two equivalents of HCl in isopropyl alcohol was added. The solution was cooled, and the resulting precipitate removed by filtration to give a pink slid (10.0 g); m.p. 305°–307° C.

ANALYSIS: Calculated for C$_{23}$H$_{34}$Cl$_2$N$_2$O$_2$: C, 62.57; H, 7.76; N, 6.34. Found: C, 62.30; H, 7.70; N, 6.04.

Example 9

2-(4-Hydroxy-2-methylanilino)-1,3,4,6,7,11$\beta$-hexahydro-2H-benzo[$\alpha$]quinolizine monooxalate monohydrate (TR 3356).

A mixture of 4'-hydroxy-o-acetotoluidide (94.7 g; 0.57 mole), benzylbromide (97.5 g; 0.57 mole); and K$_2$CO$_3$ $_3$78.8 g; 0.57 mole) in 1 L of dry acetone was stirred at reflux for 48 hours. Approximately 400 ml of acetone was removed by distillation, and 1 L of 10% NaOH was added. The remaining acetone was removed by distillation, the reaction mixture was cooled, and then filtered to give a white solid (258.0 g). The solid was transferred to a separatory funnel, and EtOAc (1 L) was added. The resulting mixture was washed with water (4×500 ml), 10% NaOH (6×400 ml), water (2×200 ml), and saturated NaCl (2×500 ml). The EtOAc solution was boiled and Skelly C was added until crystals became to form. The mixture was cooled and filtered to give feathery, white needles (104.5 g), m.p. 135°–136° C. A sample of this material (8.0 g) was recrystallized twice from a mixture of benzene and Skelly C to give white needles (7.0 g) m.p. 130°–131° C.

ANALYSIS: Calculated for C$_{16}$H$_{17}$NO$_2$: C, 75.27; H, 6.71; N, 5.48. Found: C, 75.63; H, 6.79; N, 5.44.

A solution of 4'-(benzyloxy)-o-acetotoluidide (104.5 g) in 1 L of 20% KOH in EtOH was heated at reflux for 24 hours. Approximately 600 ml of EtOH was removed by distillation, and then 1 L of water was slowly added. The reaction mixture was distilled until the distillate became cloudy, cooled, and then extracted with CHCl$_3$ (5×100 ml). The combined CHCl$_3$ extracts were dried (MgSO$_4$) and evaporated in vacuo to give a dark oil (91.3 g). The oil was distilled to give 4-benzyloxy-2-methylaniline (79.0 g; b.p. 145° C.) as a clear, colorless oil which crystallized to a white solid on standing. A solution of 1,3,4,6,7,11$\beta$-hexahydro-2H-benzo[$\alpha$]-quinolizine-2-one (20.1 g; 0.1 mole), 4-benzyloxy-2-methylaniline (23.5 g; 0.11 mole), and a catalytic amount of p-toluenesulfonic acid in 300 ml of benzene was heated at reflux (24 hours) using a Dean-Stark trap to remove water. The solvent was evaporated in vacuo to give the imine as a dark oil. The oil was dissolved in MeOH (200 ml) and stirred in an ice-bath as NaBH$_4$ (20.0 g) was added portionwise. After 1.5 hours the ice-bath was removed and the reaction mixture slowly exothermed to reflux temperature. The resulting solution was cooled and evaporated in vacuo, and the residue was stirred with a mixture of water (300 ml) and CHCl$_3$ (100 ml). The resulting two layers were separated, and the aqueous layer extracted with CHCl$_3$ (4×50 ml). The combined CHCl$_3$-extracts were washed with water (2×100 ml) and saturated NaCl (2×100 ml), dried (MgSO$_4$), and evaporated in vacuo to give a dark oil. The oil was dissolved in Et$_2$O, treated with activated carbon, then filtered. To the Et$_2$O filtrate was added a solution of oxalic acid (18.0 g) in acetone. The purple solid which formed upon cooling was removed by filtration and dissolved in a boiling mixture of isopropyl alcohol (600 ml) and MeOH (100 ml). Upon cooling a mixture of a tan solid and dark oil formed. The mixture was reheated to boiling and the oil redissolved. The tan solid remained suspended and was removed by filtration from the hot solution to give a tan solid (7.8 g), m.p. 200°–202° C. The solid was recrystallized twice from a mixture of water and DMF to give a tan solid (4.0 g), m.p. 211°–212° C.

ANALYSIS: Calculated for $C_{29}H_{32}N_2O_5$: C, 71.29; H, 6.60; N, 5.73. Found: C, 71.36; H, 6.63; N, 5.72.

To a sample of 2-(4-benzyloxy-2-methylanilino)-1,3,4,6,7,11β-hexahydro-2H-benzo[α]quinolizine monooxalate (10.0 g; 0.02 mole) was added 100 ml of MeOH, 50 ml of DMF, and 2.0 g of 10% Pd/C. The reaction mixture was hydrogenated at 50 pounds/inch², and the calculated amount of $H_2$ was taken up in 24 hours. The catalyst was removed by filtration, and the filtrate was evaporated in vacuo to give an oil which crystallized upon addition of $Et_2O$. The solid was removed by filtration and recrystallized from a mixture of MeOH, DMF, and isopropyl alcohol to give a white solid (1.0 g) m.p. 179°–181° C.

ANALYSIS: Calculated for $C_{22}H_{28}N_2O_6$: C, 63.44; H, 6.77; N, 6.72. Found: C, 65.09; H, 6.92; N, 6.66.

Example 10

2-(3,4-Dihydroxyanilino)-1,3,4,6,7,11β-hexahydro-2H-benzo[α]-quinolizine monooxalate (TR 3358).

A solution of 1,3,4,6,7,11β-hexahydro-2H-benzo[α]-quinolizine-2-one (10.0 g; 0.05 mole), 3,4-bisbenzyloxyaniline (15.3 g; 0.05 mole), and a catalytic amount of p-toluenesulfonic acid in 300 ml of benzene was heated at reflux (24 hours) using a Dean-Stark trap to remove water (0.9 ml). The solvent was evaporated in vacuo to give the imine as a dark oil. The imine was dissolved in MeOH (200 ml) and stirred in an ice-bath as $NaBH_4$ (10.0 g) was added portionwise. After 1 hour the ice-bath was removed, the reaction mixture heated at reflux for 1 hour, then cooled. The solvent was evaporated in vacuo, and the resulting residue was stirred with a mixture of water (200 ml) and $Et_2O$ (200 ml). The resulting two layers were separated, and the aqueous layer extracted with $Et_2O$ (2×100 ml). The combined $Et_2O$ extracts were washed with water (2×100 ml) and saturated NaCl (2×100 ml), dried ($MgSO_4$), and evaporated in vacuo to give a dark oil. The oil was dissolved in $Et_2O$ and treated with activated carbon then filtered. To the filtrate were added two equivalents of HCl in isopropyl alcohol. The purple precipitate which formed was removed by filtration and recrystallized three times from a mixture of MeOH and $Et_2O$ to give a white solid (4.3 g), which slowly melts with above 197° C.

ANALYSIS: Calculated for $C_{33}H_{36}Cl_2H_2O_2$: C, 70.33; H, 6.44; N, 4.97. Found: C, 70.12; H, 6.41; N, 4.74.

To a solution of 2-(3,4-bisbenzyloxyanilino)-1,3,4,6,7,11β-hexahydro-2H-benzo[α]quinolizine (7.5 g; 0.015 mole) in a mixture of DMF (50 ml) and MeOH (100 ml) was added 3.0 g of 10% Pd/C and oxalic acid (1.4 g; 0.015 mole). The reaction mixture was hydrogenated at 50 pounds/inch², and the calculated amount of $H_2$ was taken up in 24 hours. The catalyst was removed by filtration, and the filtrate was evaporated in vacuo to give an oil which solidified on standing. The solid was recrystallized from MeOH to give a white solid (2.0 g), m.p. 155°–160° C.

ANALYSIS: Calculated for $C_{21}H_{24}N_2O_6$: C, 62.99; H, 6.04; N, 7.00. Found: C, 61.70; H, 6.08; N, 6.77.

Example 11

Coronary Vasodilating Effects of the Compounds of This Invention

The coronary vasodilating effects of the compounds of this invention were determined in the mongrel dogs of either sex, anesthetized intravenously with pentobarbital. Under artificial respiration with room air, the thorax was opened at the fifth left intercostal space, the pericardium was incised, and the circumflex branch of the left coronary artery was dissected. An electromagnetic flowmeter sensor was applied around the artery for continuous recording of blood flow. Systemic blood pressure was recorded from a cannulated femoral artery, and coronary resistance calculated by dividing pressure by flow. Compounds were administered intravenously at a dose of 1 mg/kg.

Table II shows that the compounds elicited an increase in coronary blood flow and a concomitant decrease in coronary resistance, both effects lasting for about 60 minutes. None of the compounds changed systemic blood pressure appreciably. In contrast, the prior art compound produced a long-lasting decrease in systemic blood pressure and coronary flow, without modifying resistance.

TABLE II

EFFECTS OF BENZOQUINOLIZINE DERIVATIVES ON CORONARY FLOW AND RESISTANCE IN THE OPEN-CHEST ANESTHETIZED DOG.

| Example No. | Compound | Parameter | Per Cent Change At | | | | | |
|---|---|---|---|---|---|---|---|---|
| | | | 10 min | 20 min | 30 min | 40 min | 50 min | 60 min |
| 2 | TR 3273 | Coronary Flow | +48 | +60 | +60 | +40 | +24 | +12 |
| | | Coronary Resistance | −38 | −39 | −36 | −27 | −19 | −11 |
| | | Blood Pressure | −9 | −2 | +2 | +2 | 0 | 0 |
| 4 | TR 3245 | Coronary Flow | +20 | +25 | +30 | +30 | +25 | +15 |
| | | Coronary Resistance | −25 | −23 | −20 | −17 | −13 | −7 |
| | | Blood Pressure | −10 | −4 | +4 | +8 | +8 | +7 |
| 3 | TR 3210 | Coronary Flow | +36 | +30 | +21 | +9 | +3 | −6 |
| | | Coronary Resistance | −39 | −28 | −17 | −6 | +4 | +17 |
| | | Blood Pressure | −17 | −6 | 0 | +2 | +7 | +10 |
| II* | 4-methoxy Prior Art | Coronary Flow | +4 | −4 | −11 | −19 | −19 | −19 |
| | | Coronary Resistance | −14 | −7 | −8 | +3 | +7 | +.6 |
| | | Blood Pressure | −11 | −11 | −18 | −16 | −13 | −14 |

*2-(4-methoxyanilino)-1,3,4,6,7,11β-hexahydro-2H-benzo[α]quinolizine.

What is claimed is:
1. A compound having the formula

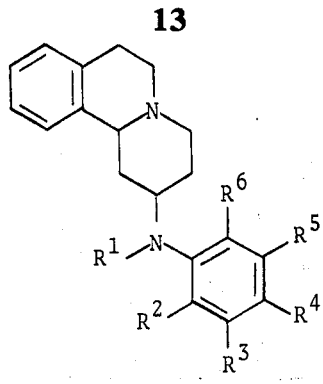

or a non-toxic pharmacologically acceptable salt thereof wherein:

R¹ is selected from the group consisting of hydrogen or an alkanoyl group having from 2 to 4 carbon atoms; and each of substituents R², R³, R⁴, R⁵, and R⁶ is selected from the group consisting of hydrogen, methyl, or hydroxyl provided that at least one of said substituents is hydroxyl.

2. The compound of claim 1, 2-(2-hydroxyanilino)-1,3,4,6,7,11β-hexahydro-2H-benzo[α]quinolizine dihydrochloride.

3. The compound of claim 1, 2-(3-hydroxyanilino)-1,3,4,6,7,11β-hexahydro-2H-benzo[α]quinolizine dihydrochloride.

4. The compound of claim 1, 2-(4-hydroxyanilino)-1,3,4,6,7,11β-hexahydro-2H-benzo[α]quinolizine monoxalate monohydrate.

5. The compound of claim 1, 2-(4-hydroxyanilino)-1,3,4,6,7,11β-hexahydro-2H-benzo[α]quinolizine dihydrochloride.

6. The compound of claim 1, 2-(2,4-dihydroxyanilino)-1,3,4,6,7,11β-hexahydro-2H-benzo[α]-quinolizine dihydrobromide hydrate.

7. The compound of claim 1, 2-(2,6-dihydroxyanilino)-1,3,4,6,7,11β-hexahydro-2H-benzo[α]-quinolizine hydrochloride.

8. The compound of claim 1, 2-(3,4-dihydroxyanilino)-1,3,4,6,7,11β-hexahydro-2H-benzo[α]-quinolizine monooxalate.

9. The compound of claim 1, 2-(2-methyl-4-hydroxyanilino-1,3,4,6,7,11β-hexahydro-2H-benzo[α]-quinolizine monooxalate monohydrate.

10. The compound of claim 1, 2-(2,3,5,6-tetramethyl-4-hydroxyanilino)-1,3,4,6,7,11β-hexahydro-2H-benzo[α]quinolizine dihydrochloride monohydrate.

11. The compound of claim 1, N-(4-hydroxyphenyl)-N-(1,3,4,6,7,11β-hexahydro-2H-benzo[α]quinolizin-2-yl)propionamide hydrochloride.

12. In a therapeutic method of producing coronary vasodilation by administration by conventional means of a coronary vasolidating agent to an individual in whom that therapy is indicated, the improvement which comprises:

administering to the individual an effective coronary vasodilating amount of a compound having the formula

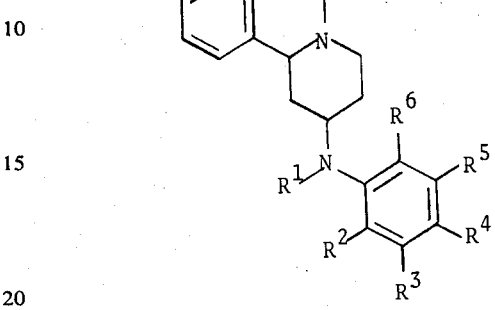

or a non-toxic pharmacologically acceptable salt of said compound wherein:

R¹ is selected from the group consisting of hydrogen or alkanoyl having from 2 to 4 carbon atoms; and each of substituents R², R³, R⁴, R⁵, and R⁶ is selected from the group consisting of hydrogen, methyl, or hydroxyl such that at least one of said substituents is hydroxyl.

13. The method of claim 12, in which said compound is 2-(4-hydroxyanilino)-1,3,4,6,7,11β-hexahydro-2H-benzo[α]-quinolizino monoxalate monohydrate.

14. The method of claim 12, in which said compound is 2-(4-hydroxyanilino)-1,3,4,6,7,11β-hexahydro-2H-benzo[α]-quinolizine dihydrochloride.

15. The method of claim 12, in which said compound is 2-(2,4-dihydroxyanilino)-1,3,4,6,7,11β-hexahydro-2H-benzo[α]quinolizine dihydrobromide hydrate.

16. The method of claim 12, in which said compound is 2-(2,6-dihydroxyanilino)-1,3,4,6,7,11β-hexahydro-2H-benzo[α]quinolizine hydrochloride.

17. The method of claim 12, in which said compound is 2-(3,4-dihydroxyanilino)-1,3,4,6,7,11β-hexahydro-2H-benzo[α]quinolizine monooxalate.

18. The method of claim 12, in which said compound is 2-(2-methyl-4-hydroxyanilino)-1,3,4,6,7,11β-hexahydro-2H-benzo[α]quinolizine monooxalate monohydrate.

19. The method of claim 12, in which said compound is 2-(2,3,5,6-tetramethyl-4-hydroxyanilino)-1,3,4,6,7,11β-hexahydro-2H-benzo[α]quinolizine dihydrochloride monohydrate.

20. The method of claim 12, in which said compound is N-(4-hydroxyphenyl)-N-(1,3,4,6,7,11β-hexahydro-2H-benzo[α]quinolizin-2-yl)propionamide hydrochloride.

* * * * *

UNITED STATES PATENT AND TRADEMARK OFFICE
CERTIFICATE OF CORRECTION

PATENT NO. : 3,995,041
DATED : November 30, 1976
INVENTOR(S) : Herbert John Havera et al It is certified that error appears in the above-identified patent and that said Letters Patent are hereby corrected as shown below:

First page, Line 4 of title and Line 2 of Abstract; Column 1, Lines 4, 9 and 41; Column 2, Line 50; Column 3, Lines 2, 45 and 54; Column 4, Lines 60 and 64; Column 5, Lines 20, 21, 56 and 58; Column 6, Lines 21, 22, 64 and 67; Column 7, Lines 34 and 35; Column 8, Lines 2, 20 and 50; Column 9, Lines 41 and 43; Column 10, Lines 4 and 38; Column 11, Lines 4, 20 and 21; Column 12, Line 6 and line below Table II; Column 13, Lines 26, 29, 32, 36, 39, 42, 45, 48, 52 and 54; Column 14, Lines 33, 36, 39, 42, 45, 48, 52 and 56; in each instance change "$\alpha$" to -- a --.

Column 3, Line 1, After "11", change "$\alpha$" to -- $\beta$ --.
Column 6, Line 36, Change "HaHCO$_3$" to -- NaHCO$_3$ --.
Column 6, Line 40, Change "3.32" to -- 3.21 --.
Column 6, Line 60, Before "7.71", change "H" to -- N --.
Column 10, Line 8, Before "78.8", delete subscript "3", second occurrence.
Column 11, in Example 3 of Table II, delete "4 methoxy".

Signed and Sealed this

Fifth Day of September 1978

[SEAL]

Attest:

RUTH C. MASON
Attesting Officer

DONALD W. BANNER
Commissioner of Patents and Trademarks